United States Patent [19]

Buchanan

[11] Patent Number: 5,083,029
[45] Date of Patent: Jan. 21, 1992

[54] MEASURING WATER CONTENT BY NEUTRON THERMALIZATION

[75] Inventor: Ronnie J. Buchanan, Duncan, Okla.

[73] Assignee: Halliburton Company, Duncan, Okla.

[21] Appl. No.: 650,370

[22] Filed: Feb. 4, 1991

[51] Int. Cl.$^5$ .......................................... G01N 23/222
[52] U.S. Cl. ............................ 250/390.05; 250/390.04
[58] Field of Search .................. 290/390.05, 390.01, 290/390.04, 390.06

[56] References Cited

U.S. PATENT DOCUMENTS

| | | | |
|---|---|---|---|
| 3,213,280 | 10/1965 | Burley et al. | 250/390.05 |
| 3,354,310 | 11/1967 | Swift | 250/390.5 |
| 3,532,883 | 10/1970 | Dresia et al. | 250/390.05 |
| 4,645,635 | 2/1987 | Yuen et al. | 250/390.5 |
| 4,766,319 | 8/1988 | Regimand | 250/390.5 |

OTHER PUBLICATIONS

"Model 2500X Coke Moisture System" for Kay-Ray Inc., (1982).
"Model 4100F Coke Drum Level Measurement System" Kay-Ray Inc. (1982).
"Level Measurements Eased With Hand-Held Instrument" Printed in Chemical Processing Publication, Dated Nov. 1986.
"6500 Mass Flowmeter-The Unique New System That Simultaneously Measures Density, Flow and Mass Flow " for Kay-Ray Inc. (1980).

Primary Examiner—Janice A. Howell
Assistant Examiner—Richard Hanig
Attorney, Agent, or Firm—James R. Duzan; E. Harrison Gilbert, III

[57] ABSTRACT

A vessel for receiving a test sample of fluid whose water content is to be determined and a thermal neutron sensor are retained in cavities of a biological radioactivity shield. The cavities are lined with a material which blocks external thermal neutrons outside the test sample from being detected by the thermal neutron sensor. Another cavity, having an inner end terminated by the lining material, receives a source of fast neutrons which are to be emitted through the liner into the test sample to become thermal neutrons if they interact with hydrogen within the test sample. The latter thermal neutrons which are backscattered to the sensor are detected, and in response an electrical signal encoded to represent the count of detected thermal neutrons is generated to indicate a measure of the water content of the test sample.

15 Claims, 3 Drawing Sheets

MEASURING WATER CONTENT BY NEUTRON THERMALIZATION

BACKGROUND OF THE INVENTION

This invention relates generally to apparatus and methods for measuring water content by neutron thermalization. This invention relates more specifically to a particular apparatus and method for measuring water content of a cement slurry to be used in an oil or gas well.

In the oil and gas industry, it is often necessary to know the water concentration of a fluid being pumped through a pipe. This is particularly needed for a cement slurry which is to be pumped into a well for cementing a casing or a liner into place and for a fracturing fluid which is to be pumped into a well for fracturing a formation. Presently, water content of cement slurries and fracturing fluids is determined based on measured density.

Measurements of water content based on density are, however, not necessarily accurate indications of actual water content in lightweight or air-entrained fluids. In these types of fluids, a small change in density can be related with a large change in water content. To measure the large change in water content, the small change in density would have to be measured accurately. This is particularly difficult to do with the density measuring devices presently used in the oil and gas industry.

Rather than rely on density measurements which might not have the precision or accuracy needed for accurate water content determinations, it would be desirable to measure the water content directly. In a system where water is the only source of hydrogen, water content can be determined by sensing the attenuation of neutrons emitted across a short distance of the material because the attenuation is proportional to the number of hydrogen atoms in the material. The neutron attenuation technique has, however, the following shortcomings with regard to measuring water content of a cement slurry or fracturing fluid to be used in an oil or gas well: low response (i.e., a low count rate per unit neutron emitted per second) and interference from other elements in the slurry or fluid.

Particularly for materials with relatively low water content, microwave systems have been used to measure water content directly. This technique can be used where the ionic content of the water is relatively constant and the electrical conductivity of the solids in the material is low.

In view of the foregoing, there is the need for an improved technique for measuring water content of a substance, such as a cement slurry or fracturing fluid to be used in an oil or gas well.

SUMMARY OF THE INVENTION

The present invention overcomes the above-noted and other shortcomings of the prior art by providing a novel and improved apparatus and method for measuring water content of a fluid by detecting thermal neutrons backscattered from hydrogen atoms contained in the water constituent of a tested fluid. More specifically, the present invention measures water content of a cement slurry in a pipe by detecting the neutrons from a source mounted on the outside of the pipe that are thermalized and scattered into a thermal neutron detector also mounted on the outside of the pipe. It is contemplated that the present invention is suitable for measuring water content of other substances, such as fracturing fluids, for example.

The present invention measures water content directly and is not substantially affected by other substances in the fluid. This provides for a more correct measurement of water content than by first measuring density and then calculating the water content.

The present invention is nonintrusive. A vessel, such as a pipe, is used to retain or direct a test sample of the fluid through the apparatus of the present invention, and all the other components of the apparatus of the invention are mounted on the outside of the vessel.

The present invention can be used to provide real time readout of water content. This can be used in automatically controlling blending or pumping units used in making or pumping the tested fluid.

The present invention is relatively insensitive to air entrained in the fluid as compared to the results obtained from the density measurement technique.

The present invention does not require any other sampling or analysis of the fluid.

The apparatus of the present invention generally comprises: a vessel for receiving a substance whose water content is to be measured; sensor means for sensing thermalized neutrons; a thermal neutron absorber disposed around the vessel and the sensor means; means for emitting fast neutrons through the thermal neutron absorber into the vessel; and a biological shield encasing the sensor means, the thermal neutron absorber, and the means for emitting and extending around the vessel. The present invention is, however, specifically directed to an apparatus for measuring water content of a cement slurry. This specific apparatus comprises: a radiation shield having defined therein a first cavity, spaced second and third cavities intersecting the first cavity, and a fourth cavity intersecting the first cavity in between the second and third cavities; a liner having a high thermal neutron capture characteristic, which liner is disposed in the first, second and third cavities and across the fourth cavity where the fourth cavity intersects the first cavity; a pipe disposed in the lined first cavity, which pipe is adapted to be connected to receive a flow of the cement slurry; a first thermal neutron detector, disposed in the lined second cavity to provide a signal in response to sensed thermal neutrons; a second thermal neutron detector, disposed in the lined third cavity to provide a signal in response to sensed thermal neutrons; and a fast neutron source disposed in the fourth cavity to emit fast neutron through the liner and the pipe into cement slurry in the pipe so that at least some of the fast neutrons can interact with hydrogen in the cement slurry within the pipe to become thermalized and backscattered for detection by the first and second detectors.

The present invention also provides a method of measuring water content in a substance, comprising: putting into a non-hydrogenous pipe a test sample of a substance containing water as its only hydrogenous constituent; emitting fast neutrons, from a source of neutrons including a radioactive material selected from the group consisting of americium-beryllium and californium, into the test sample so that fast neutrons are thermalized in response to the amount of hydrogen in the test sample; detecting, with a detector disposed adjacent the pipe at an angle to the source of neutrons within the range between 20 degrees and 60 degrees, thermalized neutrons backscattered from hydrogen in the test sample and generating in response thereto a signal representative of the amount of hydrogen, and thus of the water, in the test sample; preventing thermalized neutrons outside the test sample of the fluid from being detected during the step of detecting, including absorbing thermal neutrons outside the test sample in a liner disposed around the pipe and the detector, the liner including a high thermal neutron capture element selected from the group consisting of boron and cadmium; and shielding the environment s outside the liner with a body including poly-boron, the body encasing the source of neutrons, the detector and the liner and extending around the pipe.

Therefore, from the foregoing, it is a general object of the present invention to provide a novel and improved apparatus and method for measuring water content of a substance, such as specifically a cement slurry for an oil or gas well. Other and further objects, features and advantages of the present invention will be readily apparent to those skilled in the art when the following description of the preferred embodiment is read in conjunction with the accompanying drawings.

DETAILED DESCRIPTION OF PREFERRED EMBODIMENT

Figure 1:
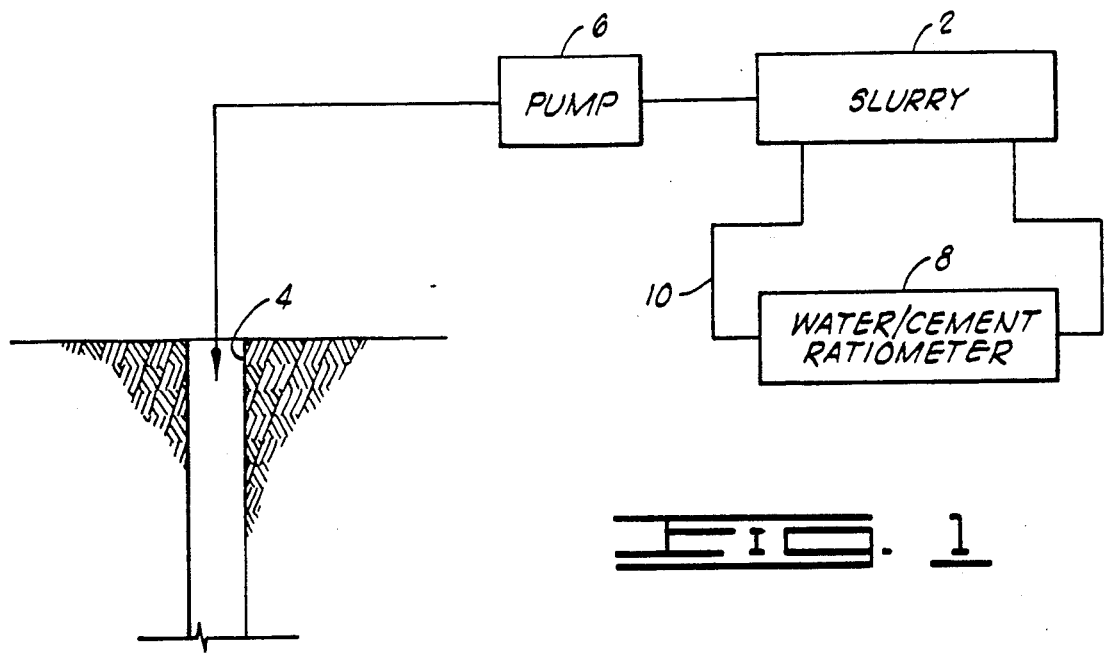
FIG. 1 is a block diagram of a system with which the present invention can be used.

The preferred embodiment of the present invention is particularly suitable for measuring water content of a cement slurry to be pumped into an oil or gas well; however, it is contemplated that it is suitable for other substances, such as fracturing fluids, for example. Referring to FIG. 1, a tub 2 contains a cement slurry whose water content needs to be known to ensure the slurry is suitable for the particular environment of a well 4 into which the slurry is to be pumped by a pump 6. The tub 2, the blending or mixing system of which it is a part, and the pump 6 are conventional types known in the art. To determine the water content of the slurry, the apparatus of the present invention, identified in FIG. as a water/cement ratiometer 8, is connected into a conventional recirculation line 10 connected to the tub 2.

Figure 2:
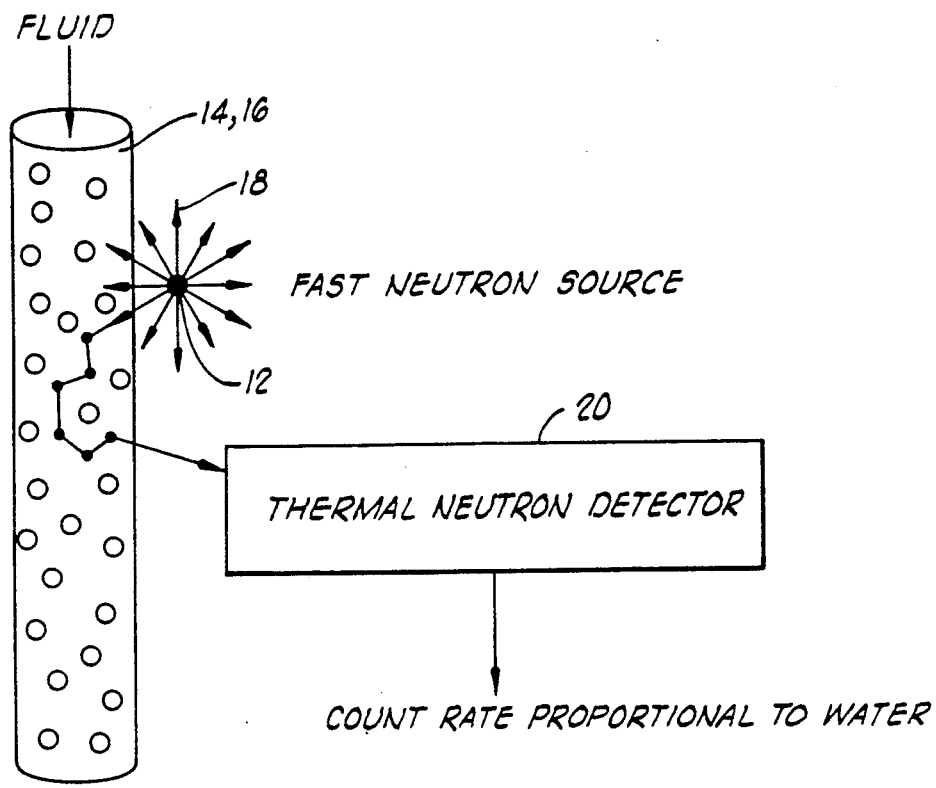
FIG. 2 is a schematic and block diagram illustrating the apparatus and method of the present invention.
Figure 3:
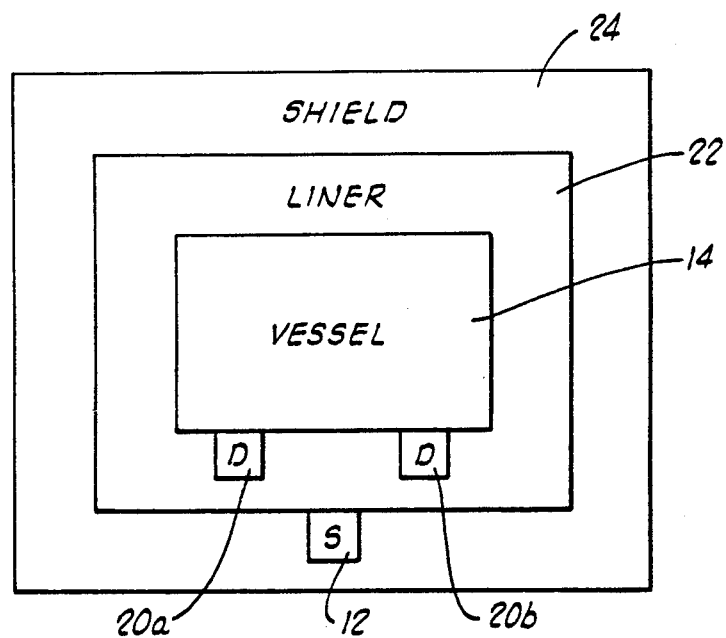
FIG. 3 is a block diagram of the preferred embodiment apparatus of the present invention.

Referring to FIGS. 2 and 3, an overview of the water/cement ratiometer 8 constituting the apparatus of the present invention will be given. This apparatus is used in performing the preferred embodiment method of the present invention.

A fast neutron source 12 mounted on the outside of a vessel 14, such as a pipe 16, emits fast neutrons 18, at least some of which transgress the vessel 14. The neutrons that transgress the vessel 14 have a probability of interacting with the atoms in the fluid, namely the cement slurry for the FIG. 1 environment, in the vessel 14. Because a fast neutron loses the most energy when it interacts with a nucleus of approximately its own mass, i.e., a proton, it is readily degraded to thermal energies in the presence of a hydrogenous material, such as water. In comparison, the energy losses resulting from interactions with heavier elements, such as are found in cement and sand in a cement slurry, are small; therefore, insignificantly few fast neutrons are thermalized due to these other constituents.

Thermalized neutrons from within the substance in the vessel 14 are detected by a thermal neutron sensor 20 mounted on the outside of the vessel 14. The thermal neutron sensor 20 is selected so that its response is high for thermal neutrons but falls off rapidly with increasing neutron energy. This allows for selectively detecting neutrons thermalized by the hydrogen in the water of the tested cement slurry and rejecting those that are only degraded in energy by heavier elements.

The resulting count rate of the thermalized neutrons detected by the sensor 20 is a function of the water content of the fluid in the vessel 14 when the water is the only hydrogenous constituent of the fluid and the vessel 14. The count rate is in the form of an encoded signal generated by the sensor 20. This signal is sent to an instrument for automatically calculating water content through predetermined calibration factors. Such instrument and predetermined calibration factors are conventional as known in the art.

Referring to FIG. 3, the vessel 14 and the thermal neutron sensor 20, comprising in the preferred embodiment two detectors 20a, 20b, are wrapped in a thermal neutron absorber having a high thermal neutron capture characteristic. This prevents neutrons thermalized outside the vessel 14 from interfering with the measurement made on the fluid in the vessel 14. In the preferred embodiment, the absorber includes a liner 22 disposed in a biological shield 24 which protects the environment outside the liner 22 by blocking outwardly emitted neutrons.

Figure 4:
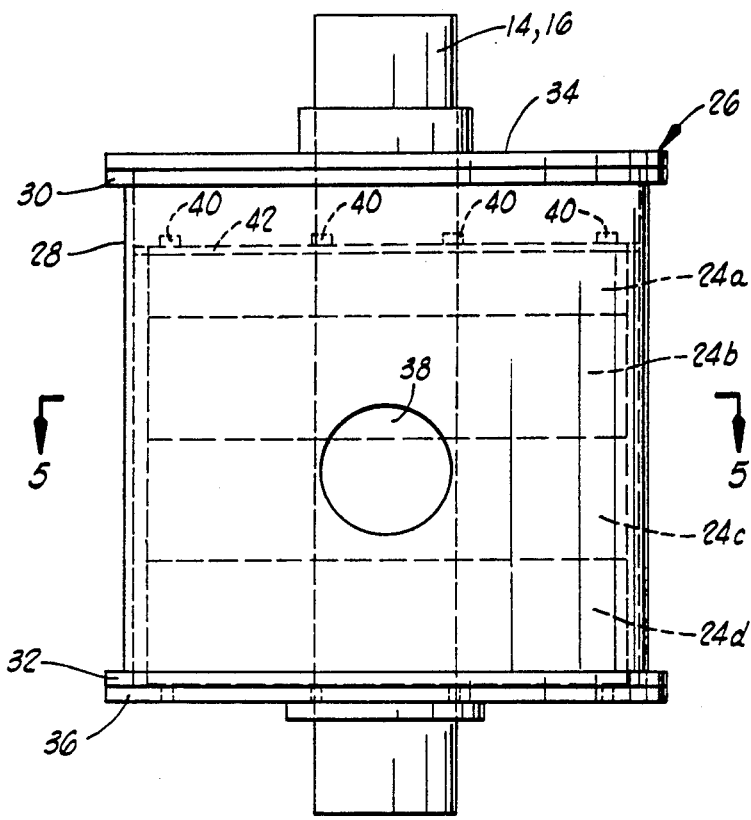
FIG. 4 is an exterior elevational view of a particular implementation of the preferred embodiment apparatus of the present invention.
Figure 5:
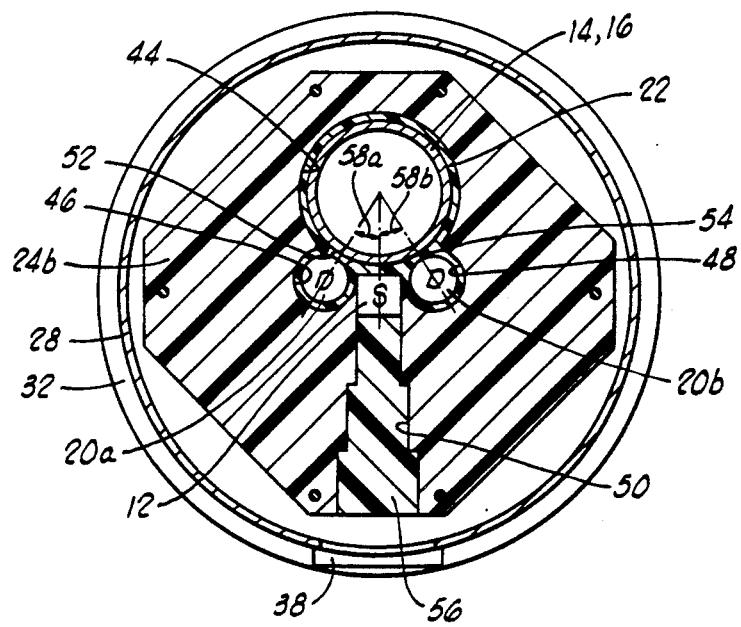
FIG. 5 is a sectional plan view of the particular implementation as taken along line 5—5 in FIG. 4.

A particular implementation of the apparatus depicted in FIGS. 2 and 3 is shown in FIGS. 4 and 5. In addition to the elements depicted in FIGS. 2 and 3, the particular implementation also includes a protective housing 26. The housing 26 includes a cylindrical steel jacket 28 having flanges 30, 32 at its opposite ends. The interior of the jacket 28 is hollow for receiving the other components of the apparatus, but the ends are closed by plates and collars 34, 36. The pipe 16 passes through the jacket 28 and openings in the plates and collars 34, 36. The interior of the jacket 28 is accessible through a covered, lockable porthole 38.

Seated inside the hollow interior of the housing 26 is the biological radiation shield 24. In the particular implementation of FIGS. 4 and 5, the shield 24 is made of four blocks 24a, 24b, 24c, 24d of a material referred to herein as poly-boron (i.e., a boron-containing polymer wherein the polymer slows the neutrons and the boron is in a sufficient concentration to capture the slowed neutrons). A specific poly-boron is a series 200 5% borated polyethylene (polyethylene with 5% boron) from Reactor Experiments in California. These blocks have the square shape with the truncated corners as shown in FIG. 5, but in general the blocks can have other shapes or be replaced by a single block or other configuration. These blocks are connected by bolts 40 and a retaining plate 42 to define a rigid body having a maximum lateral dimension of approximately fourteen inches in the particular implementation. In the rigid shield body four cavities 44, 46, 48, 50 are milled by suitable means known in the art. Although the particular implementation of the preferred embodiment shield 24 includes poly-boron as the neutron blocking element, it is contemplated that other shielding materials such as paraffin, water or oil can be used.

The cavities 44, 46, 48 defined in the shield 24 have cylindrical shapes which are parallel and contiguous. That is, the cavities 46 and 48, although spaced from each other, intersect the cavity 44. At each intersection, there is an opening. The opening between the cavities 44, 46 is marked in FIG. 5 with the reference numeral 52, and the opening between the cavities 44, 48 is marked in FIG. 5 with the reference numeral 54. The cavities 44, 46, 48 are radially offset from the centerline of the shield 24 a sufficient distance to permit the source 12 of fast neutrons to be positioned near the center of the shield 24.

The cavity 50 intersects the cavity 44 in between the cavities 46, 48, but the cavity 50 is perpendicular to the cavity 44. The cavity 50 shown in FIG. 5 is formed of cylindrical counterbores which have been filled with a polyboron plug 56 after the apparatus has been assembled as further described hereinbelow. The inner end of the cavity 50 is terminated by a portion of the liner 22 as shown in FIG. 5.

The liner 22 not only extends across the cavity 50 where the cavity 50 intersects the cavity 44, but the liner 22 also extends around the surfaces of the cavities 44, 46, 48. The openings 52, 54 where the cavities 44, 46 and 44, 48, respectively, intersect are wide enough so that they are not completely filled by the liner 22 at the lines of intersection of the respective cavities. That is, gaps still exist so that the lined cavities 46, 48 remain in communication with the lined cavity 44.

In the particular implementation, the liner 22 is made of Flex/Boron from Reactor Experiments. This is a flexible sheet which has a high concentration of boron and which can be manually put in place in the cavities 44, 46, 48 and across the inner end of the cavity 50 once they are milled in the shield 24. This embodiment of the liner 22 is ⅛ inch thick. I have found that this is sufficient to adequately block external thermal neutrons from entering the cavities 44, 46, 48. For the specific application of measuring water content in a cement slurry, the liner 22 is limited to a material having a high thermal neutron capture element selected from the group consisting of boron and cadmium.

Once the shield 24 has been built and the liner 22 installed, the pipe 16 embodying the vessel 14 in the particular implementation, the source 12 and the sensor 20 are installed.

The pipe 16 is inserted into the lined cavity 44. The pipe 16 of the particular implementation is made of a suitable non-hydrogenous material. That is, it is made of any suitable material capable of holding or carrying the fluid to be tested, but a material which does not have hydrogen. This is important to prevent thermalization of neutrons by anything other than hydrogen in the fluid.

In the particular implementation, the pipe 16 has a nominal four-inch inner diameter which I have determined is a particularly suitable size for measuring water content of a cement slurry of the type to be used in an oil or gas well. The pipe 16 is 25 inches long and has threaded ends extending outside the housing 26 for connecting with suitable couplings into the recirculation line 10 (FIG. 1). The portion of the pipe 16 inside the cavity 44 of the shield 24 is directly surrounded by the liner 22 except for the gaps at openings 52, 54 where the cavities 46, 48 intersect the cavity 44; however, the liner 22 extends around the detectors 20a, 20b so that this interior portion of the pipe 16 is completely enclosed around its cylindrical side. The liner 22 separates the pipe 16 from the source 12.

The source 12 of fast neutrons is a conventional device known to the art; however, for my particular implementation suitable for measuring water content of a cement slurry, the source 12 includes a radioactive material selected from the group consisting of americium-beryllium and californium. A particularly suitable source includes a 250-millicurie americium-beryllium material from Gammatron in Houston, Tex.

The source 12 is inserted into the cavity 50 before the cavity is closed with the plug 56. The source 12 is disposed at the inner end of the cavity 50 closed by the liner 22. Thus, when operational, the source 12 emits fast neutrons through the liner 22 and the pipe 16 into contents of the pipe 16 obtained from the tub 2 shown in FIG. 1. At least some of these fast neutrons interact with hydrogen in the contents within the pipe 16. The contents within the pipe are also referred to as the test sample, and they can be retained in or flowing through the pipe during a test when the water content is being measured. The fast neutrons that interact with the hydrogen are thermalized. The thermalized neutrons that are backscattered within the range of the sensor 20 are detected to indicate the hydrogen content of the test sample. In the cement slurries for which the present invention is particularly intended to be used (but not necessarily limited thereto), the only hydrogenous constituent is water; therefore, the detected hydrogen content is a measure of the water content of the tested substance.

The sensor 20 that senses the thermalized, backscattered neutrons includes two detectors 20a, 20b in the particular implementation of the present invention. The detector 20a is inserted into the lined cavity 46, and the detector 20b is inserted into the lined cavity 48. The detectors 20a, 20b are adjacent, but not touching, the pipe 16.

Each detector 20a, 20b can in general be any suitable type known in the art; however, for the particular implementation related to measuring water content in a cement slurry, each detector is a two-inch by six-inch helium-3, four atmosphere thermal neutron detector from Texas Nuclear. This detector generates an electrical signal encoded to indicate the count of thermalized neutrons detected.

Within the foregoing construction of my present invention, there are certain features which are critical for its proper implementation. The source 12 and the detectors 20a, 20b must be suitably matched. I have found that the aforementioned specific embodiments of the source 12 and the detectors 20a, 20b are suitable for the specific use of my invention in measuring water content in at least a cement slurry in the oil and gas industry.

Not only must the source 12 and the detectors 20a, 20b be suitably matched, but they must also be maintained in proper orientation relative to each other and relative to the pipe 16. This is achieved in the present invention by properly sizing the lined cavities 44, 46, 48, 50 and by securing the source 12 in the cavity 50 with the plug 56. This construction holds the source 12 and the detectors 20a, 20b fixed distances from the center of the pipe 16. This also holds the detectors 20a, 20b at respective fixed acute angles 58a, 58b (FIG. 5) relative to the source 12 as measured from the center of the pipe 16. In the particular implementation described hereinabove, the angles 58a, 58b are within the range between 20 degrees and 60 degrees. Preferably, the angles 58a, 58b should be as small as possible, and the source 12 and the detectors 20a, 20b should be as close as possible to the pipe 16 but for the separation caused by the liner 22.

Another critical feature of the present invention is the liner 22. It must be used and it must be adequate to prevent non-test sample produced thermal neutrons from affecting the detectors 20a, 20b. I have determined that the specific liner 22 materials referred to hereinabove are particularly suitable in an apparatus and method for measuring water content of at least a cement slurry for an oil or gas well.

Another critical feature is the shield 24. The shield 24 protects biology at the site of the apparatus, and the particular design of the shield 24 affects the response of the apparatus. The material of the shield 24 described hereinabove is particularly suitable for the apparatus and method for measuring water content of at least a cement slurry for an oil or gas well.

Once the apparatus 8 has been constructed, it is connected into the recirculation line 10 of the system shown in FIG. 1 by suitable known couplings. The slurry illustrated in FIG. 1 can then be flowed in known manner through the recirculation line 10 and thereby through the pipe 16. This puts a test sample of the hydrogenous cement slurry into the pipe 16. The cement slurries for which the particular implementation of the present invention is specifically adapted to be used contain water as their only hydrogenous constituent.

At a desired time, the source 12 is energized in a known manner to emit fast neutrons into the test sample so that the fast neutrons are thermalized in response to the amount of hydrogen in the test sample. Fast neutrons which do not interact within the test sample pass through into the shield 24.

Figure 6:
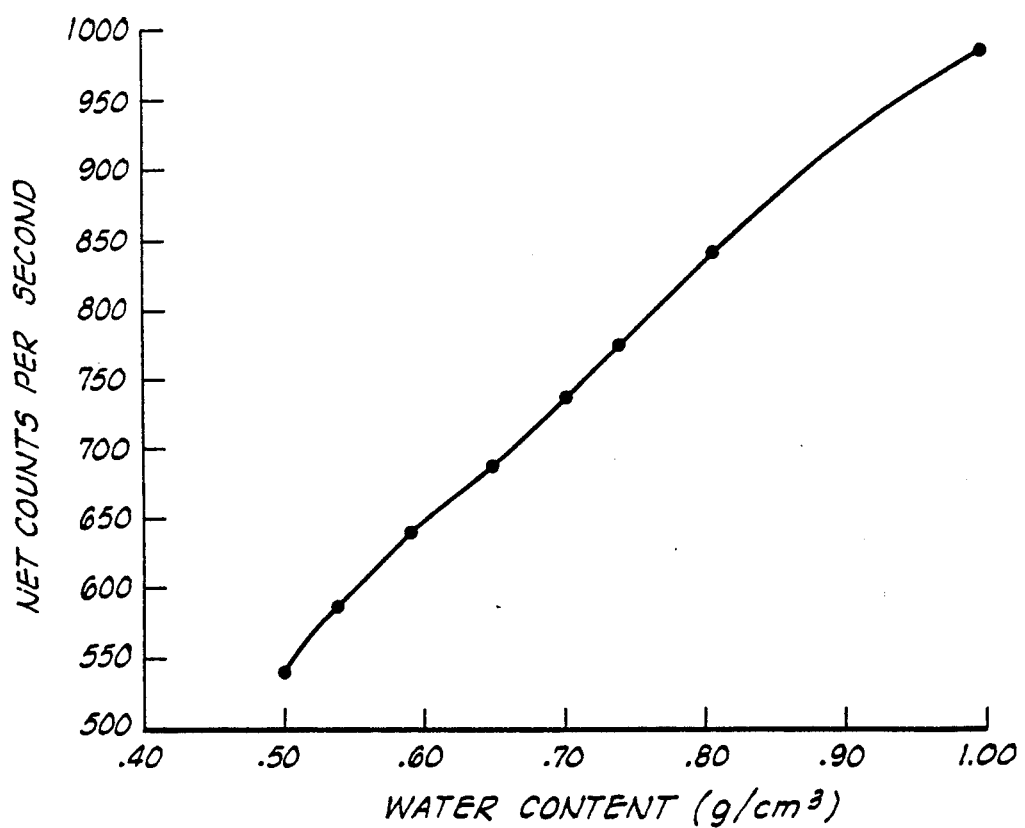
FIG. 6 is a graph showing the relationship between the count of detected thermalized neutrons and water content for a specific test.

Thermalized neutrons backscattered from the test sample are sensed by the detectors 20a, 20b. An electrical signal encoded in a known manner to indicate the count of detected thermal neutrons is generated by the detectors 20a, 20b. The indicated count is a measure of the hydrogen, and thus of the water, in the test sample. The signal can be used in a known manner to provide a particular output designating the water content. An illustration for a correlation between counts of detected thermal neutrons and water content is shown in FIG. 6. The graph of FIG. 6 was made from data obtained with a prototype which is not necessarily useful or ideal for measuring water content of a cement slurry to be used in an oil or gas well, but the illustrated correlation is pertinent. The prototype included a single helium-3 detector spaced 45 degrees from the source of a 100-millicurie americium-beryllium source disposed adjacent a four-inch inner diameter pipe in a cadmium lined four-inch poly-boron shield.

Thermalized neutrons outside the test sample are prevented from being detected by the detectors 20a, 20b by the liner 22. The liner 22 absorbs thermal neutrons produced outside the outer surface of the liner 22. Both thermal and fast neutrons are blocked by the shield 24 from escaping into the environment outside the apparatus.

Thus, the present invention is well adapted to carry out the objects and attain the ends and advantages mentioned above as well as those inherent therein. While a preferred embodiment of the invention has been described for the purpose of this disclosure, changes in the construction and arrangement of parts and the performance of steps can be made by those skilled in the art, which changes are encompassed within the spirit of this invention as defined by the appended claims.

What is claimed is:

1. An apparatus for measuring water content of a substance, comprising:
    a vessel for receiving the substance;
    sensor means for sensing thermalized neutrons;
    a thermal neutron absorber disposed around said vessel and said sensor means;
    means for emitting fast neutrons through said thermal neutron absorber into said vessel; and
    a biological shield encasing said sensor means, said thermal neutron absorber, and said means for emitting and extending around said vessel.

2. An apparatus as defined in claim 1, wherein said thermal neutron absorber includes boron.

3. An apparatus as defined in claim 1, wherein said thermal neutron absorber includes cadmium.

4. An apparatus as defined in claim 1, wherein said sensor means and said means for emitting are fixed relative to said vessel so that there is an acute angle between said sensor means and said means for emitting measured from the center of said vessel.

5. An apparatus as defined in claim 4, wherein said acute angle is within the range between 20 degrees and 60 degrees.

6. An apparatus as defined in claim 1, wherein:
    said biological shield includes a rigid poly-boron member having defined therein a first cavity and second and third cavities contiguous with said first cavity;
    said thermal neutron absorber includes a flexible member lining said first, second and third cavities, said member including a high thermal neutron capture element selected from among the group consisting of boron and cadmium;
    said vessel is disposed in said lined first cavity; and
    said sensor means includes two thermal neutron detectors disposed in said lined second and third cavities.

7. An apparatus as defined in claim 6, wherein:
    said rigid poly-boron member further has a fourth cavity defined therein, said fourth cavity having an inner end terminated by a portion of said flexible member; and
    said means for emitting is disposed in said fourth cavity adjacent said portion of said flexible member.

8. An apparatus for measuring water content of a cement slurry, comprising:
    a radiation shield having defined therein a first cavity, spaced second and third cavities intersecting said first cavity, and a fourth cavity intersecting said first cavity in between said second and third cavities;
    a liner having a high thermal neutron capture characteristic, said liner disposed in said first, second and third cavities and across said fourth cavity where said fourth cavity intersects said first cavity;
    a pipe disposed in said lined first cavity, said pipe adapted to be connected to receive a flow of the cement slurry;
    a first thermal neutron detector, disposed in said lined second cavity to provide a signal in response to sensed thermal neutrons;

a second thermal neutron detector, disposed in said lined third cavity to provide a signal in response to sensed thermal neutrons; and a fast neutron source disposed in said fourth cavity to emit fast neutrons through said liner and said pipe into cement slurry in said pipe so that at least some of the fast neutrons can interact with hydrogen in the cement slurry within said pipe to become thermalized and backscattered for detection by said first and second detectors.

9. An apparatus as defined in claim 8, wherein said radiation shield includes a rigid member including poly-boron and said liner includes a flexible member including boron.

10. An apparatus as defined in claim 8, wherein said liner includes boron.

11. An apparatus as defined in claim 8, wherein said liner includes cadmium.

12. An apparatus as defined in claim 8, wherein each of said second and third cavities is spaced from said fourth cavity at an acute angle measured from the center of said first cavity between the respective centers of said second and third cavities and the center of said fourth cavity.

13. An apparatus as defined in claim 12, wherein said acute angle is within the range between 20 degrees and 60 degrees.

14. An apparatus as defined in claim 8, wherein:
said radiation shield includes poly-boron and said first, second and third cavities are parallel;
said liner includes a high thermal neutron capture element selected from the group consisting of boron and cadmium;
said pipe has a nominal four inch inner diameter;
said first and second detectors each includes a two-inch by six-inch helium-3, four atmosphere thermal neutron detector;
said source includes a radioactive material selected from the group consisting of americium-beryllium and californium; and
said second and third cavities are each spaced from said fourth cavity by an angle within the range between 20 degrees and 60 degrees.

15. A method of measuring water content in a substance, comprising:
putting into a non-hydrogenous pipe a test sample of a hydrogenous substance containing water as its only hydrogenous constituent;
emitting fast neutrons, from a source of neutrons including a radioactive material selected from the group consisting of americium-beryllium and californium, into the test sample so that fast neutrons are thermalized in response to the amount of hydrogen in the test sample;
detecting, with a detector disposed adjacent the pipe at an angle to the source of neutrons within the range between 20 degrees and 60 degrees, thermalized neutrons backscattered from hydrogen in the test sample and generating in response thereto a signal representative of the amount of hydrogen, and thus of the water, in the test sample;
preventing thermalized neutrons outside the test sample of the fluid from being detected during said step of detecting, including absorbing thermal neutrons outside the test sample in a liner disposed around the pipe and the detector, the liner including a high thermal neutron capture element selected from the group consisting of boron and cadmium; and
shielding the environment outside the liner with a body including poly-boron, the body encasing the source of neutrons, the detector and the liner and extending around the pipe.

* * * * *